(12) United States Patent
Moonen et al.

(10) Patent No.: US 8,231,557 B2
(45) Date of Patent: Jul. 31, 2012

(54) ASSEMBLY FOR HEAT TREATING BIOLOGICAL TISSUE

(75) Inventors: Chretien Theophilus Willibrordus Moonen, Gradignan (FR); Rares Salomir, Chaponost (FR); Charles Mougenot, Bordeaux (FR); Jean Palussiere, Bordeaux (FR)

(73) Assignee: Koninklijke Philips Electronics N.V., Eindhoven (NL)

( * ) Notice: Subject to any disclaimer, the term of this patent is extended or adjusted under 35 U.S.C. 154(b) by 1055 days.

(21) Appl. No.: 11/587,800

(22) PCT Filed: Apr. 28, 2005

(86) PCT No.: PCT/EP2005/051926
§ 371 (c)(1),
(2), (4) Date: Oct. 9, 2007

(87) PCT Pub. No.: WO2005/107869
PCT Pub. Date: Nov. 17, 2005

(65) Prior Publication Data
US 2008/0114274 A1    May 15, 2008

(30) Foreign Application Priority Data
Apr. 29, 2004  (FR) ..................... 04 04562

(51) Int. Cl.
*A61H 1/00*  (2006.01)
(52) U.S. Cl. ..................... 601/3; 601/2; 601/4
(58) Field of Classification Search .......... 600/407, 600/411, 439; 601/2–4; 606/27–31; 607/96, 607/98–105
See application file for complete search history.

(56) References Cited

U.S. PATENT DOCUMENTS

| | | | |
|---|---|---|---|
| 4,397,314 A | 8/1983 | Vaguine | |
| 5,368,031 A | 11/1994 | Cline et al. | |
| 5,485,839 A | 1/1996 | Aida et al. | |
| 6,128,522 A | 10/2000 | Acker et al. | |
| 6,350,276 B1 | 2/2002 | Knowlton | |
| 6,458,121 B1 | 10/2002 | Rosenstock et al. | |
| 6,823,216 B1 | 11/2004 | Salomir et al. | |
| 2003/0019681 A1 | 1/2003 | Nakamura | |
| 2004/0010289 A1 | 1/2004 | Biggs et al. | |
| 2004/0176680 A1 | 9/2004 | Moonen et al. | |

FOREIGN PATENT DOCUMENTS
WO    WO 02085457 A1 * 10/2002

OTHER PUBLICATIONS

Salomir, R, et al, Local Hyperthermia with MR-Guided Focused Ultrasound: Spiral trajectory of the focal point optimized for temperature uniformity in the target region. Journal of Magnetic Resonance Imaging, 12:571-583. (2000).*

* cited by examiner

*Primary Examiner* — Brian Casler
*Assistant Examiner* — Daniel Huntley (57) ABSTRACT

An assembly for heat treating an area of biological tissue, including an energy generating device for supplying energy to a focal point in said area, a device for measuring the spatial temperature distribution in said area, and a control unit for controlling the movement of the focal point along a predetermined path to give a spatial temperature distribution consistent with a pre-sent distribution, characterized in that, as the focal point moves along the path, the control unit controls the distribution of the energy provided by the generating device depending on the measured temperature distribution and the pre-set distribution, in accordance with a control law including a proportional-integral-derivative term.

21 Claims, 8 Drawing Sheets

ASSEMBLY FOR HEAT TREATING BIOLOGICAL TISSUE

This application is a National Stage application of PCT/EP2005/051926, filed Apr. 28, 2005, which claims priority from French patent application FR 0404562, filed Apr. 29, 2004. The entire contents of each of the aforementioned applications are incorporated herein by reference.

The area of the invention relates to the treatment of biological tissues by hyperthermia.

Hyperthermia therapies are techniques routinely used for the local treatment of biological tissues. They consist of heating a target area of the biological tissue using an energy source (laser, microwave, radiofrequency waves, ultrasound).

Generally, therapy by local hyperthermia allows medical treatment with minimum invasion. Among the types of energy used, focused ultrasound (FUS) is of particular interest since it enables a target area to be heated non-invasively and in-depth in the tissues.

During the treatment, the temperature of the target area and its immediate surrounding area must be precisely and continuously monitored. However the rise in temperature generated by ultrasound in tissues is difficult to assess since this temperature rise is dependent on biological and physiological characteristics (absorption, heat diffusion) of the tissue in the target area.

Document FR 2 823 678 (published on 25 Oct. 2002) describes an assembly for heat treatment which can be used for automatic temperature control in a target area of the tissue to be treated. The assembly comprises an ultrasound generator, MRI imaging means to measure and record spatial temperature distribution in the target region, and a control unit comprising dot-by-dot digital processing means of spatial temperature distribution. The control unit commands the movement in space of the ultrasound generator in relation to temperature distribution measured by imaging means so that the temperature in the target region follows a set temperature profile.

The document "Local hyperthermia with MR-guided focused ultrasound: Spiral trajectory of the focal point optimized for temperature uniformity in the target region", Journal of Magnetic Resonance Imaging, 12: 571-583 (published in 2000) describes a treatment method using focused ultrasound whose purpose is to obtain uniform temperature rise in a target region of large volume. According to this method, the focal point of an ultrasound generator is moved along a first spiral-shaped trajectory. Spatial temperature distribution in the target region is measured by MRI. In relation to the spatial distribution obtained, a second spiral trajectory is determined in which the speed of movement of the focal point is modified to offset non-homogeneities in temperature distribution remaining after the first trajectory. The focal point of the ultrasound generator is moved along this second trajectory.

However, said method is based on linear modelling of tissue behaviour. Yet some tissues may have non-linear behaviour, in particular with respect to their heat conduction characteristics. This may result in unstable temperature servo-control.

One purpose of the invention is to provide a stable treatment device, having good tolerance to estimation uncertainties regarding physiological parameters.

For this purpose, the invention proposes a heat treatment assembly for treating a biological tissue region comprising:
energy generating means to supply energy at a focal point of the region,
means for measuring spatial temperature distribution in said region,
a control unit able to command movement of the focal point along a predetermined trajectory with a view to obtaining a spatial distribution of temperature conforming to a set distribution.
characterized in that during the displacement of the focal point, the control unit is able to command the distribution of energy supplied by the generator means along the length of the trajectory in relation to measured temperature distribution and set distribution, in accordance with a control law comprising a Proportional-Integral-Derivative term.

The control law used in this treatment assembly makes it possible to reach a pre-defined set temperature profile in an extended target region, in spite of any non-linear physiological effects during treatment.

In one embodiment of the treatment assembly, the control unit is able to command the movement of the focal point along a series of successive trajectories and for each trajectory to command corresponding energy distribution, in relation to a set distribution associated with this trajectory and to temperature distributions measured throughout the preceding trajectories.

In this embodiment, the control unit is able to command the movement of the focal point along a first trajectory and to deduce thereupon, in relation to the measured temperature rise, a thermal diffusion coefficient D in the target region. The control unit is able to take this thermal diffusion coefficient into account in the control law.

In one embodiment of the invention, to command energy distribution, the control unit is able to determine a distribution function defining the position of the focal point along the trajectory in relation to time.

In one embodiment of the invention, the control unit is able to command the displacement of the focal point at a plurality of discrete sonication points distributed along the trajectory. The control unit is able to command the energy generating means so that at each sonication point they deposit a given quantity of energy that is the same from one sonication point to another. In this embodiment, it is the distribution of the sonication points on the trajectory which determines the distribution of energy deposited in the target region.

The invention also relates to a method for heat treating an area of biological tissue in which the energy generating means supply energy to a focal point in said region, measuring means measure spatial temperature distribution in said region, and a control unit commands the movement of the focal point along a pre-determined trajectory with a view to obtaining a spatial temperature distribution conforming to a set distribution, characterized in that during the movement of the focal point the control unit commands the distribution of energy supplied by the generating means along the trajectory in relation to measured temperature distribution and to the set distribution in accordance with a control law comprising a Proportional-Integral-Derivative term.

Other characteristics and advantages will become apparent from the following description which is purely illustrative and non-limiting, and is to be read with respect to the appended figures in which.

Figure 1:
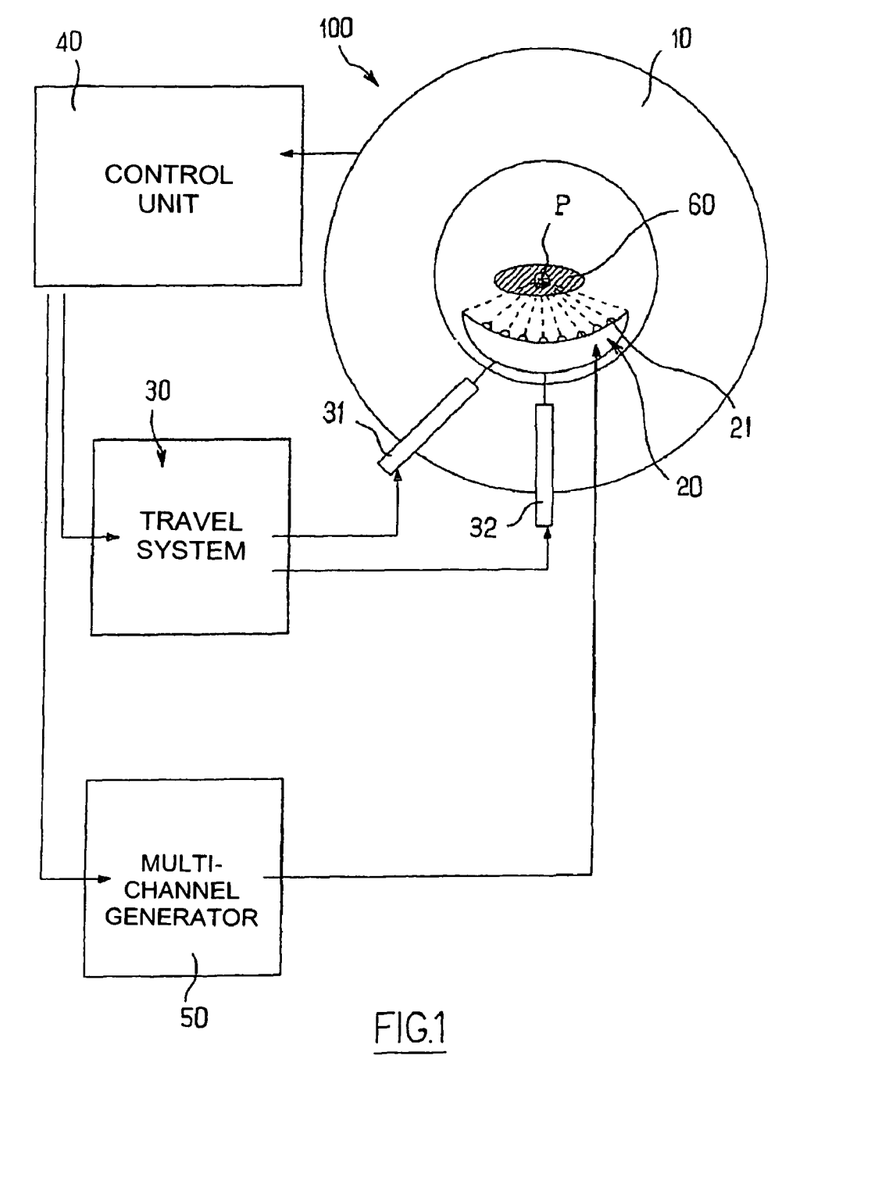
FIG. 1 schematically shows an example of a heat treatment assembly conforming to one embodiment of the invention, FIG. 2 schematically illustrates the treatment steps performed by the heat treatment assembly, FIG. 3 gives examples a and b of spatial profiles of set-point temperatures such as they can be commanded for a trajectory of spiral shape.

In FIG. 1, the treatment assembly 1 shown comprises MRI imaging apparatus including a magnet 10. The assembly 1 comprises energy generating means in the form of an annular-array probe 20 and a multi-channel generator 50 supplying the annular array probe 20. The probe 20 is integrated in the bed of magnet 10 and comprises generating elements 21 able to emit ultrasounds in the direction of a focal point P when the probe is supplied by the generator 50.

The annular-array probe 20 is for example a probe manufactured by Ultrasonic (Besançon, France) having a radius of 80 mm, an opening diameter of 96 mm and a variation in focal distance of between 60 and 110 mm along the vertical axis. The ultrasound generating elements 21 are able to emit at a frequency of approximately 1.5 MHz.

The energy generating means 20 can travel in the horizontal plane by means of a hydraulic travel system 30 with pistons 31 and 32 available from LEP (Paris, France). This travel system 30 has laser guiding means and its maximum travel speed is in the order of 3 mm per second, its effective speed being 2 mm per second.

Assembly 1 also comprises a control unit 40 including a central unit whose input is able to receive data from the MRI imaging apparatus and, in relation to such data, is able to command the travel system 30 to modify the focal point P of the annular-array probe 20.

When in operation, the heat treatment assembly 1 is used to treat a target region 60 of patient tissue. The control unit 40 commands the multi-channel generator 50 and the travel system 30 to perform the steps shown FIG. 2.

Initially, the energy generating means 20 are arranged with respect to the patient so that the focal point P is positioned at a point O located substantially in the centre of the target region 60 to be treated.

Figure 2:
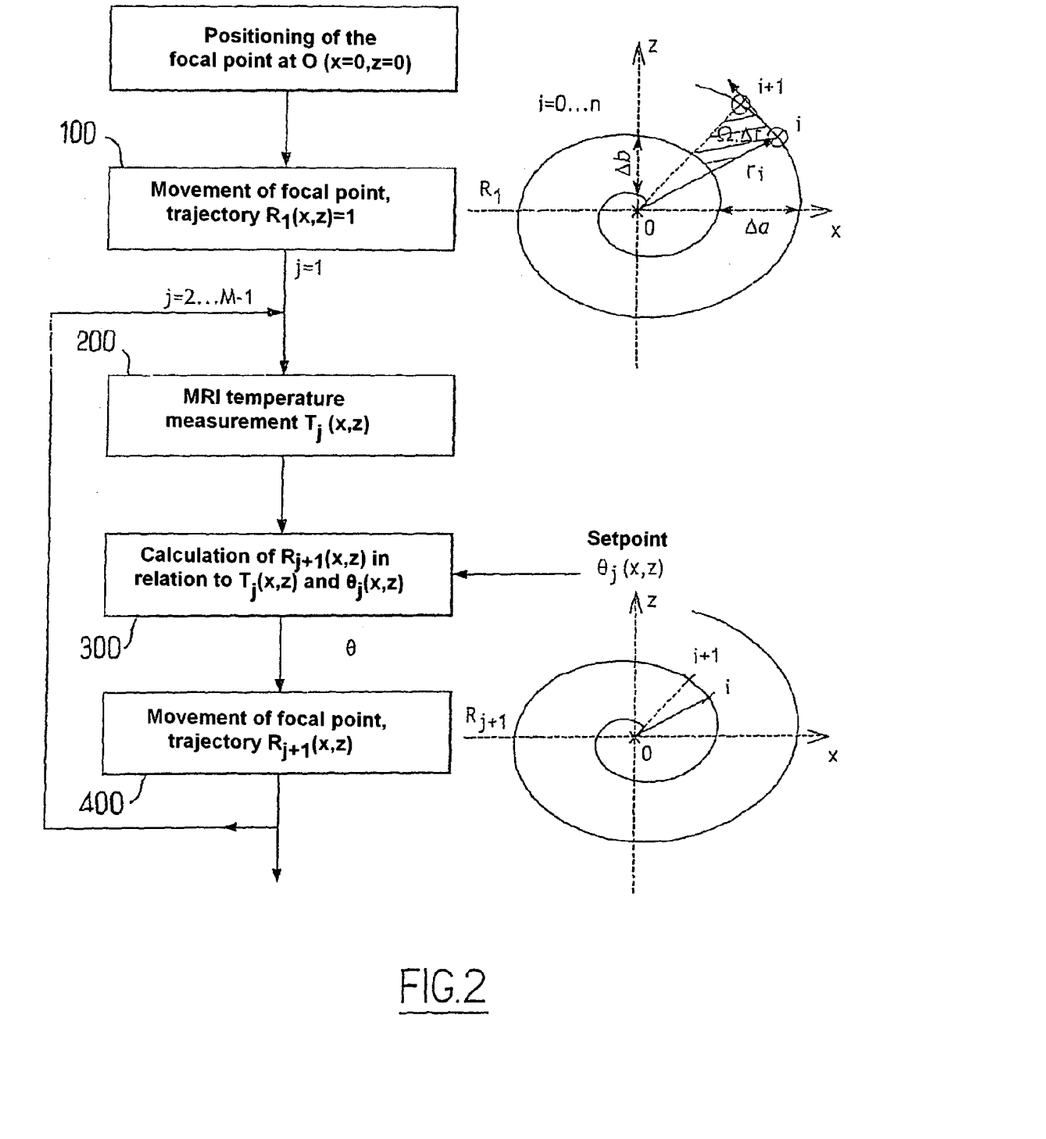

FIG. 2 schematically illustrates the treatment steps performed by the heat treatment assembly 1.

During a first step 100, the control unit 40 commands the travel system 30 to position the focal point of the energy generating means successively at a plurality of sonication points along the first predetermined trajectory (j=1). The trajectory is of general elliptical shape starting at the centre O of the target region and extending outwardly from this area. In addition, the control unit 50 commands the energy generating means 20 so that, at each point of the plurality of sonication points along the trajectory, they apply a quantity of given energy. The spiral shape of the trajectory allows energy to be deposited starting at the centre O of the target region 60 and gradually extending out to the edges of the target region. It will be understood that said spiral trajectory promotes heat diffusion from the centre of the target region towards the edges of this area and enables benefit to be drawn from this diffusion to control temperature rise in the target region.

At a reference point (Ox, Oz) whose origin is the centre O of the target region 60, the parametric equation of the trajectory of focal point P can defined as follows:

$$\begin{cases} x(\xi) = \Delta a \cdot \dfrac{\xi}{2\pi} \cdot \cos(\xi) \\ z(\xi) = \Delta b \cdot \dfrac{\xi}{2\pi} \cdot \sin(\xi) \end{cases} \quad [1]$$

in which (x, z) are coordinates of the focal point at reference point (Ox, Oz), $\Delta a$ and $\Delta b$ are the spaces between successive turns respectively following axes Ox and Oz, and $\xi$ is the parameter of the trajectory lying between O and $2\pi \cdot N$, N being the number of turns of the ellipse.

During the first trajectory, the focal point P is moved so that the area $\Omega$ added per unit of time to the region already treated is constant. This coordination translates as the following differential equation with respect to time t:

$$\xi \cdot d\xi = \dfrac{2\pi \cdot \Omega}{\varepsilon \cdot (\Delta a)^2} dt \quad [2]$$

in which $\Omega$ is the area added per unit of time to the region already covered by the spiral trajectory and $\varepsilon$ equals $\Delta b/\Delta a$ and defines the eccentricity of the ellipse.

This first elliptical trajectory is formed of a plurality of discrete sonications i, i ranging from 0 to n, whose positions with respect to the centre O of the ellipse are defined by the vectors $r_i=(x_i,z_i)$ in which $i \in [0,n]$. The focal point moves from one sonication position i at position $r_i$ to the next i+1 at position $r_{i+1}$ at a regular rate. The duration of sonication $\Delta t$ is constant from one sonication point to the next.

During a second step 200, the imaging apparatus measures the temperature distribution obtained $T_1(x,z)$ in the target region.

If the tissues of the target region were fully homogeneous, i.e. the heat absorption and diffusion characteristics are uniform in the entire target region, the trajectory performed during the first step 100 would lead to a uniform increase in temperature in the target region.

Yet this is not the case, since treated tissues are generally not homogeneous.

The measured temperature distribution is used to determine a mean coefficient of thermal diffusion D.

During a third step 300, the control unit, in relation to the measured spatial distribution of temperature $T_1(x,z)$, determines a second trajectory (j=2). This second trajectory has the same spiral shape as the first trajectory. However, the speed of travel of the focal point is modified according to a function of energy distribution $R_2$ dependent on position (x,z) of the focal point on the trajectory, so that:

$$\Re_2(x(\xi), z(\xi)) \cdot \xi \cdot d\xi = \frac{2\pi \cdot \Omega}{\varepsilon \cdot (\Delta a)^2} dt \qquad [3]$$

The effect of the distribution function $R_2$ is to modify the distance between two successive sonication points and hence the speed of travel of the focal point along the spiral trajectory. It is to be noted that equation [3] is reduced to equation [2] when $R_2$ is replaced by $R_1=1$ over the entire target region. The function $R_2$ is determined so as to offset non-homogeneities remaining after the first trajectory by modulating the energy density delivered locally in the target region.

The time of each individual sonication is always $\Delta t$, so that the focal point travels from one sonication point to the next at the same rate as during the first trajectory. The number n+1 of individual sonications along the spiral trajectory is always the same.

During a fourth step 400, the control unit commands the travel system to position the focal point of the energy generating means successively at a plurality of sonication points of the second trajectory.

Above-mentioned steps 200, 300 and 400 are optionally renewed to achieve a number M of successive trajectories, so as to impose a set temperature profile upon the area to be treated during a predetermined treatment time. For each j-$^{th}$ trajectory, the control unit determines a new distribution function $R_j$ and commands the travel system to cause the focal point of the energy generating means move along the j-$^{th}$ trajectory thus determined.

A general description is given below of the calculation step 300 of the distribution function $R_j$ calculated by the control unit.

It is considered that the control module commands the travel system and the energy generating means so that the focal point of the energy generating means travels over a number M of trajectories of pre-determined shape.

The following designations are used:

O a reference point in the target region, e.g. located in the centre of the target region:

(Ox,Oz) a two-dimensional reference of origin O, $\theta_j(x,z)$ the set temperature to be reached at a point (x,z) over the pathway of the j-$^{th}$ trajectory.

Tj(x,z) the temperature effectively measured at point (x,z) by the MRI imaging apparatus after completion of the j-$^{th}$ trajectory, $R_j$ the distribution function determined for the j-$^{th}$ trajectory, $G(D, \tau)$ Green's function used to evaluate a variation in temperature due to thermal diffusion D in the tissues (evaluated after the first trajectory) over a time $\tau$ lapsed between two trajectories.

Green's function is described for example in the appended document "Local hyperthermia with MR-guided focused ultrasound: Spiral trajectory of the focal point optimized for temperature uniformity in the target region", Journal of Magnetic Resonance Imaging 12: 571-583 (published in 2000). It's expression is:

$$G(D, \sigma)(r, r') = \frac{1}{2 \cdot \pi \cdot \sqrt{2 \cdot D \cdot \tau}} \cdot \exp\left(-\frac{\|r - r'\|^2}{4 \cdot D \cdot \tau}\right)$$

The efficacy of heating during the first trajectory can be expressed in the form of a coefficient $\alpha_1$ at point O:

$$\alpha_1 = \frac{\theta_1(x=0, z=0)}{T_1(x=0, z=0)}$$

The spatial profile of the set temperature is given by:

$$\theta_{j+1}(r) = \eta_{j+1} \cdot \frac{\theta_1(r)}{\alpha} \text{ où } \alpha < \eta_{j+1} \le 1 \qquad [4]$$

In this equation, the value of $\eta_{j+1}$ defines the desired trend in temperature between the j-$^{th}$ and (j+1)-$^{th}$ trajectory. $\eta_{j+1}=1$ corresponds to a stationary temperature in the target region. That is to say that the depositing of energy in the target region during the (j+1)-$^{th}$ trajectory, defined by the distribution function $R_{j+1}$ must solely offset heat losses due to heat conduction in the tissues.

The value of $\eta_j$ is fixed for each trajectory j by means of an iterative algorithm, at the maximum value (between $\alpha$ and 1) for which the required power supplied by the energy generating means does not exceed a limit technical tolerance value of the instruments. The limit tolerance value depends upon the energy generating means, this limit value is defined by the manufacturer of these energy generating means.

The temperature at a point r(x,z) which will be obtained after completion of the (j+1)-$^{th}$ trajectory can be evaluated as follows:

$$T_{j+1}(r) = [T_j \otimes G(D,\tau)](r) + \Re_{j+1}(r) \cdot \theta_1(r) \qquad [5]$$

This temperature takes into account the heat diffusion between the j-$^{th}$ and (j+1)-$^{th}$ trajectory and the new distribution of energy $R_{j+1}$. Green's function is always the same insofar as the coefficient of thermal diffusion D is assumed to be constant and the duration $\tau$ is the same for each trajectory.

One condition for automatic control is: $T_{j+1} = \theta_{j+1}$

Thereupon, it is deduced that:

$$\Re_{j+1}(r) \cdot \theta_1(r) = \theta_{j+1}(r) - [T_j \otimes G(D,\tau)](r) \qquad [6]$$

$$\Re_{j+1}(r) \cdot \theta_1(r) = [Tj(r) - [T_j \otimes G(D,\tau)](r)] + [\theta_{j+1}(r) - \theta_j(r)] + [\theta_j(r) - T_j(r)] \qquad [7]$$

This equation is the central equation of a control law of differential and proportional type. Under the invention, this expression is modified to obtain a PID control law (Proportional Integral and Differential). The equation of this PID control law then becomes:

$$\Re_{j+1}(r) = \underbrace{[T_j(r) - [T_j \otimes G(D, \tau)](r)]}_{(1)} + \qquad [8]$$

$$\underbrace{[\theta_{j+1}(r) - \theta_j(r)]}_{(2)} + a \cdot \underbrace{[\theta_j(r) - T_j(r)]}_{(3)} + \underbrace{\frac{a^2}{4} \cdot \sum_{k=0}^{j} [\theta_j(r) - T_j(r)]}_{(4)}$$

In equation [8] the first term (1) takes into account the variation in temperature due to heat diffusion in the tissues between two successive trajectories j and j+1. The second term (2) is the differential term of the control law which takes into account the additional layer added to the temperature profile by the (j+1)-$^{th}$ trajectory. The third term (3) is the proportional term of the control law which takes into account the instantaneous error between the measured temperature and the set temperature defined for the preceding j-$^{th}$ trajectory. Finally, the fourth term (4) is the integral term of the control law which takes into account the errors between measured temperature and the set temperature defined for each of the previous trajectories. The parameter α is a dimensionless magnitude related to the response time of the control loop of the travel system of the energy generating means. The response time of the control loop is 2τ/α.

It is to be noted that the greater the parameter α, the more the automatic control is sensitive to experimental noise with possible fluctuations. A recommended value for parameter α is 2(√2−1))≈0.8284. This value leads to elimination of terms (3) and (4) in equation [8] when calculating $R_2$ after the completion of the first trajectory. The response time of the control loop then becomes 2τ/α≈2.4143·τ which represents the time needed by the automatic control to correct any error in measured temperature.

Equation [8] is equal to:

$$\Re_{j+1}(r) \cdot \theta_1(r) = \theta_{j+1}(r) - [T_j \otimes G(D, \tau)](r) - \quad [9]$$

$$(1 - a) \cdot [\theta_j(r) - T_j(r)] + \frac{a^2}{4} \cdot \sum_{k=0}^{j} [\theta_k(r) - T_k(r)]$$

So that the time of a trajectory always remain constant, the trajectory can be time dilated or compressed in time to bring its duration to value τ. Simultaneously, the ultrasound power deposited by the energy generating means is re-normalized in reverse direction by a factor which is equal to the spatial average of $R_{j+1}$ in the region under consideration.

Figure 3:
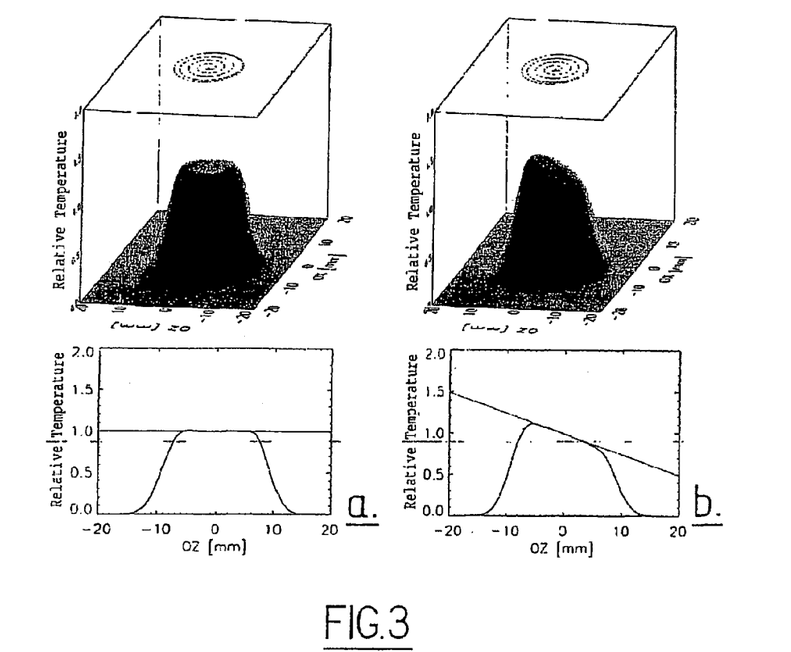

FIG. 3 shows examples a and b of spatial profiles $R_j(r) \cdot \theta 1(r)$ of set temperature such as they can be commanded for a trajectory of spiral shape. These examples are based on spiral trajectories having diameters of 12 mm and 16 mm respectively along axes Ox and Oz. The diffusion coefficient D is 0.05 mm$^2$/s. The trajectory comprises n+1=100 sonication points, the sonications being spaced apart by Δt=1.6 s. Example a relates to a function of uniform distribution $R_1(x, z)=1$, while example b corresponds to a distribution function $R_j$ having a constant slope (constant gradient along axis Ox of −0.025 mm$^{-1}$).

Figure 4:
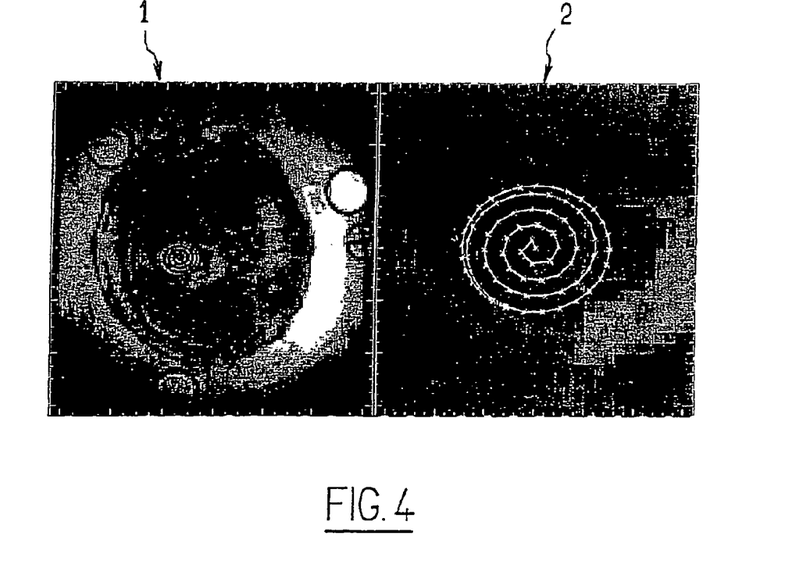
FIG. 4 shows an example of a trajectory in the form of an elliptical spiral followed by the focal point of the energy generating means, FIG. 5 comprises two diagrams respectively showing measured temperature distribution after the focal point of the energy generating means has followed a spiral trajectory, and simulated temperature distribution for a uniform thermal diffusion coefficient in the tissues to be treated.

FIG. 4 gives an example of an elliptical spiral trajectory followed by the focal point of the energy generating means. The field of vision is 128×128 mm$^2$ in image 1 whilst image 2 was magnified by a magnification of 4. The spiral trajectory has diameters of 15 mm and 11 mm respectively along axes Ox and Oz. The background image is obtained with the gradient echo sequence used for MRI thermometry. Three samples of agar gel can be seen in image 1. These samples allow three-point correction of thermometry. Inhomogeneities can be seen in the structure of the treated sample.

Figure 5:
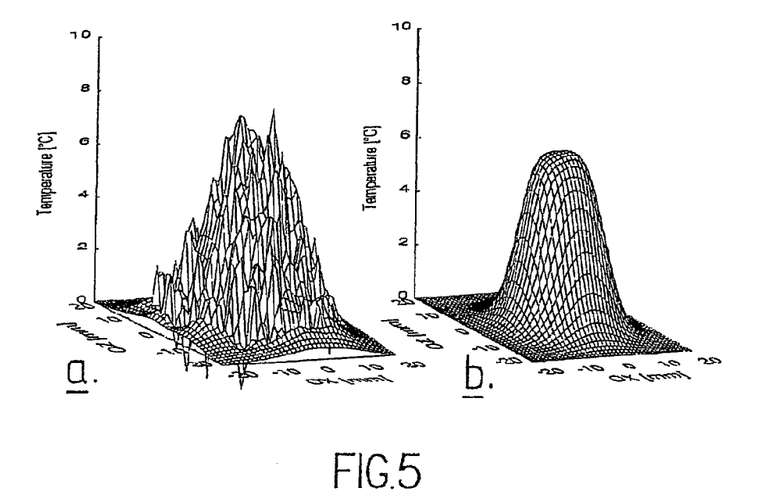

In FIG. 5 the diagram shows the distribution of measured temperature after the focal point of the energy generating means has travelled over the spiral trajectory shown FIG. 4. Diagram b shows simulated temperature distribution for a uniform coefficient of thermal diffusion D=0.13 mm$^2$/s of the tissues to be treated. Diagram b is the diagram which is the closest to the experimental profile of diagram a. This diagram b can be used to estimate the mean coefficient of thermal diffusion in the target region to be treated.

Figure 6:
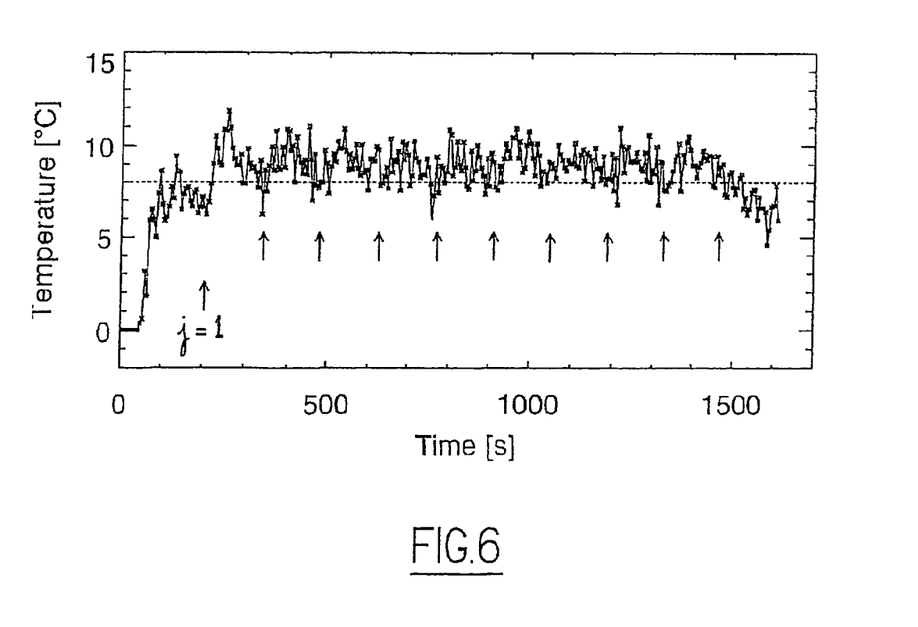
FIG. 6 is a curve showing the trend in temperature at the centre of the target region to be treated in relation to time, over a series of ten successive trajectories, the set temperature being 8° C. higher than the initial temperature in the entire target region, during an ex vivo experiment.

FIG. 6 is a curve showing the trend in measured temperature at the centre O of the target region in relation to time during ex vivo experimenting. The measured temperature changes over a series of M=10 successive trajectories. The set temperature is 8° C. in the entire target region (sublethal hyperthermia).

Figure 7:
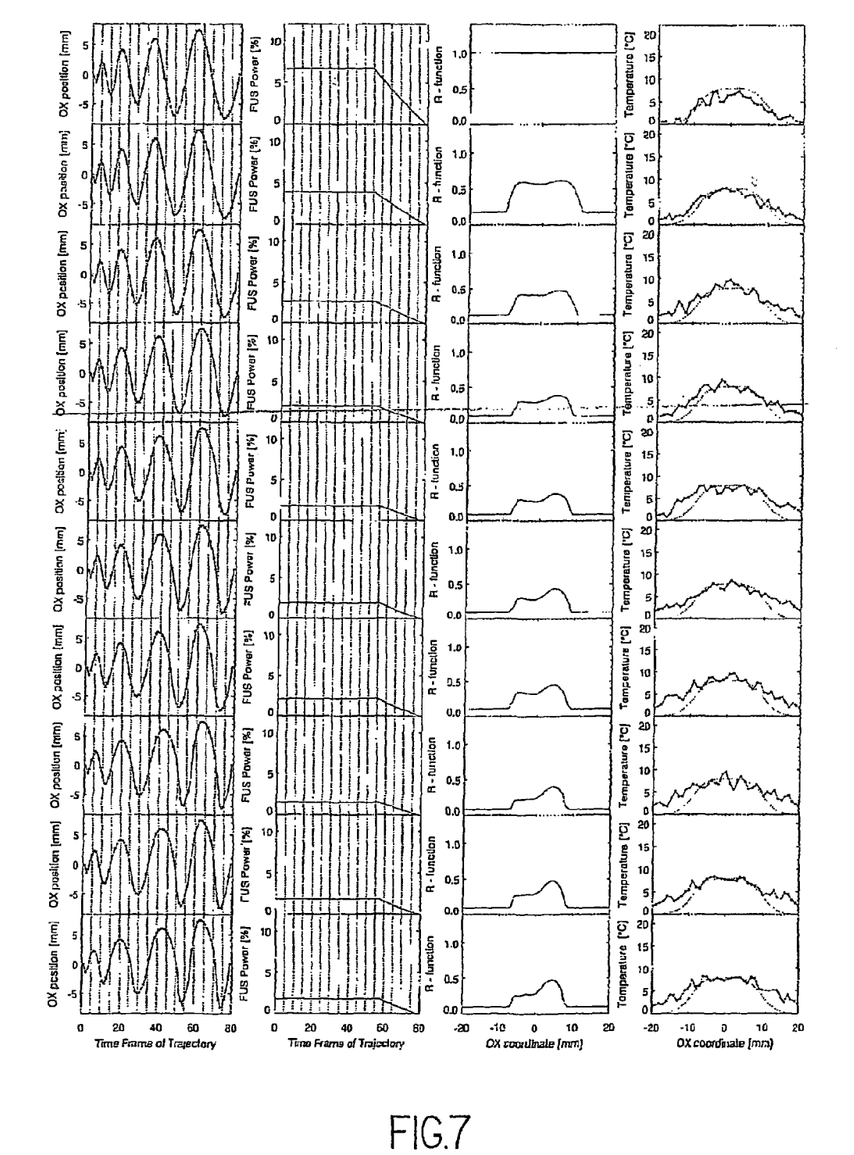
FIG. 7 shows the trend in parameters during each trajectory of the series performed for FIG. 6, these parameters comprising: a coordinate of the focal point along one of the axes (Ox) of the reference point in which the trajectory is made, the ultrasound power deposited by the energy generating means, the temperature profile measured in one section of the target region, and the temperature rise profile in the section of the target region.

FIG. 7, in column one, shows the trend of coordinate x of the focal point of each of the ten trajectories of the series conducted during the experimenting of FIG. 6. The second column indicates the ultrasound power deposited by the energy generating means during each of the trajectories. The third column gives the temperature profile measured in a section of the target region passing though point O, the centre of the target region, after each trajectory. The fourth column gives the profile of temperature rise measured in the section of the target region, obtained during each trajectory.

Figure 8:
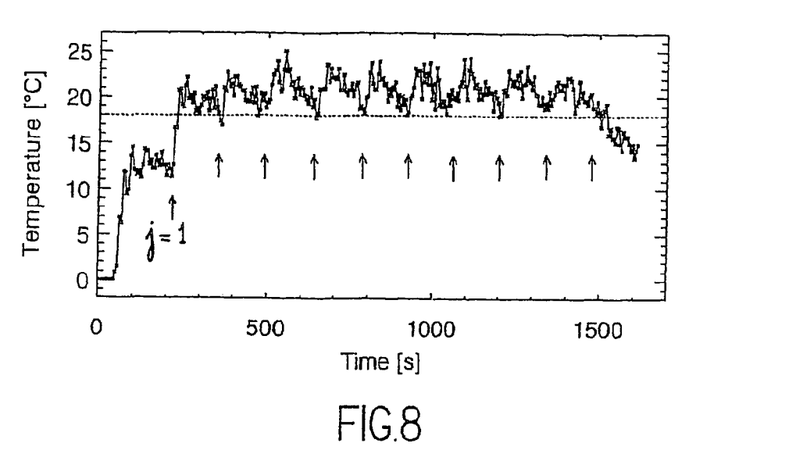
FIG. 8 is a curve showing trend in temperature at the centre of the target region to be treated in relation to time, over a series of ten successive trajectories, the set temperature being 18° C. higher than the initial temperature in the entire target region, during an ex vivo experiment.

FIG. 8 is a curve showing the trend in measured temperature at the centre O of the target region in relation to time during ex vivo experiments. The measured temperature changes over a series of M=10 successive trajectories. The set temperature is 18° C. higher than the initial temperature in the entire target region (lethal hyperthermia) for the purpose of achieving thermal ablation.

Figure 9:
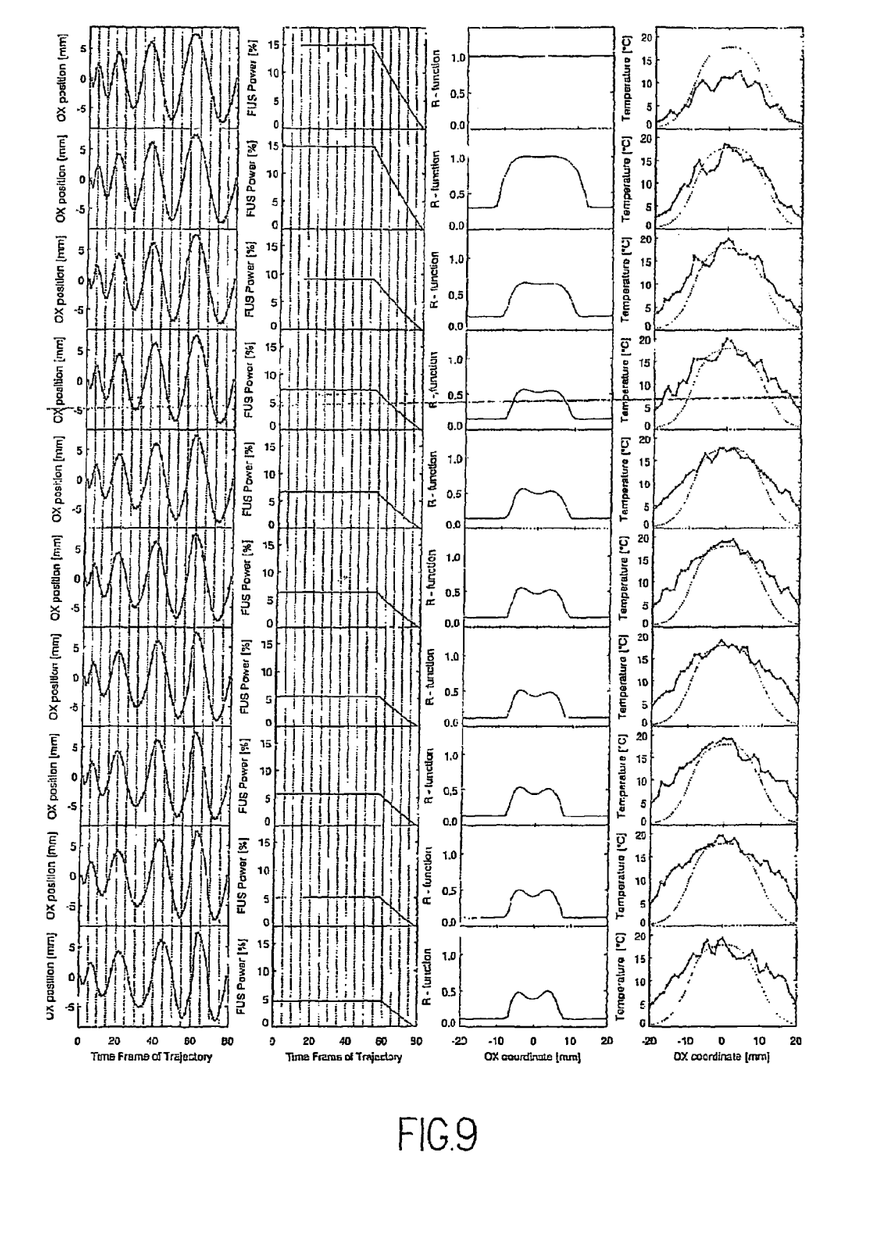
FIG. 9 shows the trend in parameters during each trajectory of the series performed for FIG. 8, these parameters comprising: a coordinate of the focal point along one of the axes (Ox) of the reference point in which the trajectory is performed, the ultrasound power deposited by the energy depositing means, the profile of energy distribution in one section of the target region, and the temperature rise profile measured in the section of the target region.

FIG. 9, in column one, shows the trend of coordinate x of the focal point of each of the ten trajectories of the series conducted during the experiments in FIG. 8. The second column indicates the ultrasound power deposited by the energy generating means during each of the trajectories. The third column shows the profile of the distribution function R calculated in a direction passing through point O, the centre of the target region, after each trajectory. The fourth column shows the profile of temperature rise measured in the section of the target region, obtained during each trajectory.

Figure 10:
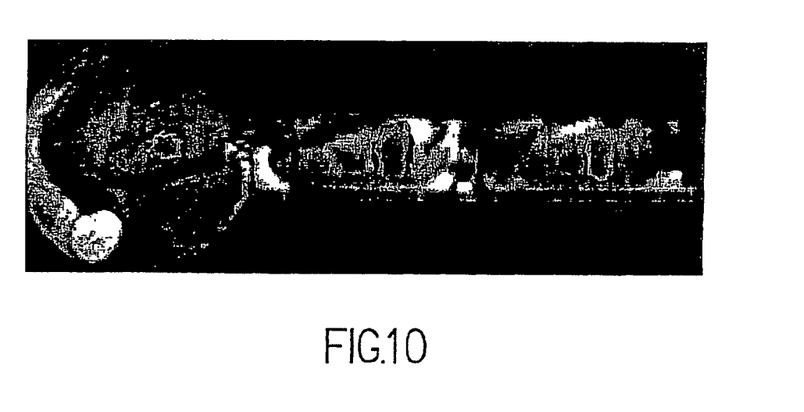
FIG. 10 is a sample three-dimensional temperature map obtained using MRI imaging apparatus.
Figure 11:
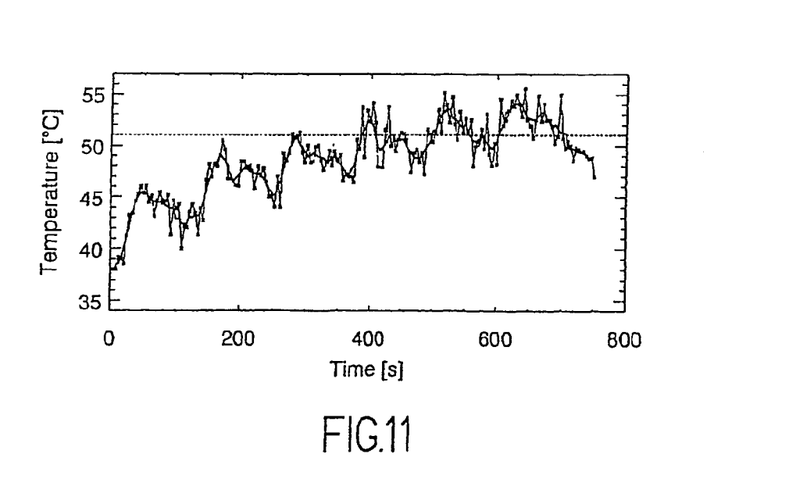
FIG. 11 is a curve showing temperature trend in the centre of the target region to be treated in relation to time, during an in vivo experiment, FIG. 12 comprises three diagrams a, b and c respectively illustrating a theoretical spiral trajectory and showing an additional turn extending outside the target region to be treated, the projection of the sonication points of the additional turn on the contour of the target region, the actual trajectory comprising the projected sonication points of the additional turn.

FIG. 10 is a sample three-dimensional temperature map obtained using MRI apparatus at the end of the sixth trajectory corresponding to FIG. 11. Experimental data was obtained with a spatial resolution of 1×1×5 mm$^3$ and smoothed by convolution with a two-dimensional Gaussian function of standard deviation of 1 mm in each direction (Ox) and (Oz). Temperature distribution cannot contain high spatial frequencies on account of thermal diffusion.

FIG. 11 is a curve showing the trend in temperature at the centre O of the target region in relation to time during in vivo experimenting (diameter of the target region: 11 mm). The measured temperature rises over a series of M=6 successive trajectories. The dotted line represents the set temperature rise (13 degrees Celsius above the physiological temperature). The difference between two successive trajectories is 2 minutes.

Figure 12:
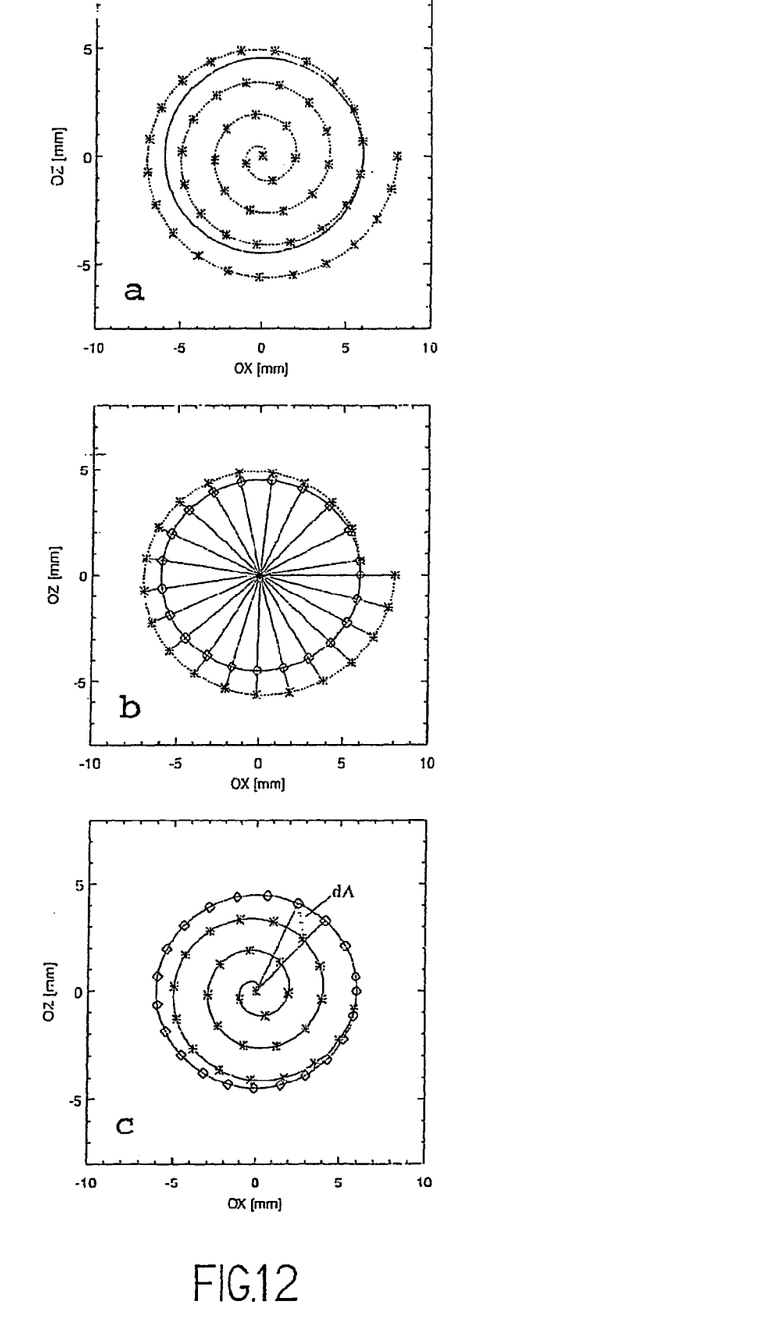

In FIG. 12 the diagram shows the positions of the different sonication points along the first trajectory (j=1) and the limits of the target region to be treated (ellipse). As can be seen in this figure, the spiral trajectory gradually covers the target region. The trajectory also comprises an additional turn which extends outside the target region. This additional turn is in fact not actually executed by the energy generating means. It is used solely to calculate the quantity of energy to be deposited at the frontier of the target region.

In FIG. 12, diagram b shows a step consisting of projecting the sonication points of the additional turn onto the contour of the target region (ellipse) in radial directions of projection.

In FIG. 12 diagram c shows the trajectory with the successive sonication points such as it will be effectively conducted by the energy generating means. This actual trajectory comprises the sonication points of the additional turn projected onto the contour of the target region.

The invention claimed is:

1. A heat treatment assembly for a region of biological tissue, comprising:
   energy generator configured to supply energy at a focal point in the region,
   a sensor configured to measure a spatial temperature distribution in said region,
   a control unit configured to control movement of the focal point along a plurality of successive predetermined trajectories for obtaining a spatial temperature distribution conforming to a set distribution, and
   during the movement of the focal point, to control distribution of the energy supplied along each trajectory of the plurality of successive predetermined trajectories in relation to the measured spatial temperature distribution and the set distribution, in accordance with a control law comprising a Proportional-Integral-Derivative term.

2. The heat treatment assembly according to claim 1, wherein the control law takes into account a coefficient of thermal diffusion of the region.

3. The heat treatment assembly according to claim 1, wherein the each trajectory includes a corresponding set distribution associated with this trajectory and to temperature distributions measured during preceding trajectories.

4. The heat treatment assembly according to claim 1, wherein the control unit is further configured to determine a distribution function defining a position of the focal point along the trajectory in relation to time.

5. The heat treatment assembly according to claim 1, wherein the control unit is further configured to move the focal point at a plurality of discrete sonication points distributed along the trajectory.

6. The heat treatment assembly according to claim 5, wherein the control unit is further configured to supply at each sonication point a given quantity of energy that is equal from one sonication point to the next.

7. The heat treatment assembly according to claim 1, wherein the control unit is further configured to control, for each trajectory, corresponding energy distribution such that:

$$\Re_{j+1}(r) \cdot \theta_1(r) = \theta_{j+1}(r) - [T_j \otimes G(D, \tau)](r) - (1-\alpha) \cdot [\theta_j(r) - T_j(r)] + \frac{a^2}{4} \cdot \sum_{k=0}^{j} [\theta_k(r) - T_k(r)]$$

in which:
$r$ is a position of a point in the region,
$\theta_1$ is a set temperature distribution to be reached during the first trajectory,
$\theta_j$ is a set temperature distribution to be reached during the $j$-$^{th}$ trajectory,
$T_j$ is a temperature distribution effectively measured by the measurement means after completion of the $j$-$^{th}$ trajectory, $G(D, \tau)$ is Green's function which depends on a thermal diffusion D in the region over a period of time $\tau$ lapsed between two trajectories $j$ and $j+1$ and
$\alpha$ is a dimensionless parameter for automatic control.

8. The heat treatment assembly according to claim 1, wherein the control unit is further configured to move the focal point along a trajectory of a general spiral shape.

9. The heat treatment assembly according to claim 1, wherein the control unit is further configured to control the movement of the focal point in relation to a set spatial temperature distribution that is uniform in the region.

10. The heat treatment assembly according to claim 1, wherein the control unit is further configured to control the movement of the focal point in relation to a set spatial temperature distribution having a uniform gradient in one direction in the region.

11. A method for heat treating a region of biological tissue, comprising the acts of:
    supplying energy to a focal point in said region,
    measuring a spatial temperature distribution in said region,
    controlling movement of the focal point along a plurality of successive predetermined trajectories to obtain a spatial temperature distribution conforming to a set distribution, and
    during the movement of the focal point, controlling a distribution of the energy supplied along each trajectory of the plurality of successive predetermined trajectories in relation to the measured temperature distribution and the set distribution, in accordance with a control law comprising a Proportional-Integral-Derivative term.

12. A method for heat treating a region of biological tissue, comprising the acts of:
    activating an energy generator to supply energy at a focal point in the region;
    measuring a spatial temperature distribution is said region;
    moving the focal point along a plurality of successive predetermined trajectories for obtaining a spatial temperature distribution conforming to a set temperature distribution; and
    during the movement of the focal point, varying a speed of travel of the focal point so as to control a distribution of the energy supplied along each trajectory of the plurality of successive predetermined trajectories as a function of a measured spatial temperature distribution and the set temperature distribution, in accordance with a control law comprising a Proportional-Integral-Derivative term.

13. The method according to claim 12, wherein the control law takes into account a coefficient of thermal diffusion of the region.

14. The method according to claim 12,
    wherein the each trajectory includes a corresponding temperature distribution associated with this trajectory and to spatial temperature distributions measured during the preceding trajectories.

15. The method according to claim 12, further comprising an act of:
    determining a distribution function defining a position of the focal point along the trajectory in relation to time so as to control distribution of the energy supplied along the each trajectory.

16. The method according to claim 12,
    wherein the act of moving moves the focal point at a plurality of discrete sonication points distributed along the trajectory.

17. The method according to claim 12,
wherein at each sonication point, the activating act supplies a given quantity of energy that is equal from one sonication point to the next.

18. The method according to claim 12,
wherein a corresponding energy distribution is controlled such that:

$$R_{j+1}(r) \cdot \theta_1(r) = \theta_{j+1}(r) - \left[ T_j \otimes G(D, \tau) \right](r) - (1-\alpha) \cdot [\theta_j(r) - T_j(r)] + \frac{a^2}{4} \cdot \sum_{k=0}^{j} \theta_k(r) - T_k(r) \right]$$

in which:

r is a position of a point in the region, $\theta_1$ is a set temperature distribution to be reached during the first trajectory, $\theta_j$ is a set temperature distribution to be reached during the j-$^{th}$ trajectory, $T_j$ is a temperature distribution effectively measured by the measurement means after completion of the j-$^{th}$ trajectory, $G(D, \tau)$ is Green's function which depends on a thermal diffusion D in the region over a period of time $\tau$ lapsed between two trajectories j and j+1, and $\alpha$ is a dimensionless parameter for automatic control.

19. The method according to claim 12, wherein the predetermined trajectory is of general spiral shape.

20. The method according to claim 12, wherein the set temperature distribution is uniform in the region.

21. The method according to claim 12, wherein the set temperature distribution has a uniform gradient in one direction in the region.

* * * * *